United States Patent [19]

White et al.

[11] Patent Number: 4,910,286

[45] Date of Patent: Mar. 20, 1990

[54] REACTIVE PHENOLIC ANTIOXIDANTS AND POLYESTERS REACTED THEREWITH

[75] Inventors: Alan W. White; Randy S. Beavers, both of Kingsport, Tenn.

[73] Assignee: Eastman Kodak Company, Rochester, N.Y.

[21] Appl. No.: 358,094

[22] Filed: May 30, 1988

[51] Int. Cl.$^4$ ............................................. C08G 63/02
[52] U.S. Cl. ........................................ 528/272; 528/98;
528/100; 528/102; 528/110; 528/112; 528/298;
528/299; 528/300; 528/302; 528/308.6;
528/370; 525/437
[58] Field of Search ............... 528/272, 298, 299, 300,
528/302, 308.6, 370, 98, 100, 102, 110, 112;
525/437

[56] References Cited

U.S. PATENT DOCUMENTS

| | | | |
|---|---|---|---|
| 3,285,855 | 11/1966 | Dexter et al. | 252/57 |
| 3,904,578 | 9/1975 | Kawase et al. | 524/334 |
| 3,989,664 | 11/1976 | Kawase et al. | 524/289 |
| 4,094,857 | 6/1978 | Wolfe | 524/227 |
| 4,171,424 | 10/1979 | Habermeier et al. | 528/292 |
| 4,704,470 | 11/1987 | Johnson | 560/137 |

FOREIGN PATENT DOCUMENTS 0150454  7/1985  European Pat. Off.

*Primary Examiner*—John Kight
*Assistant Examiner*—S. A. Acquah
*Attorney, Agent, or Firm*—J. Frederick Thomsen; William P. Heath, Jr.

[57] ABSTRACT

Disclosed are reactive phenolic compounds having the formula

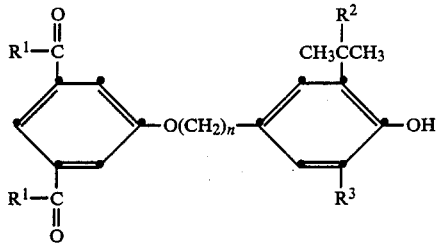

wherein $R^1$, $R^2$ and $R^3$ are certain substituents. Also disclosed are certain polyesters normally susceptible to oxidative degradation having copolymerized therein at least one residue of one of the phenolic compounds.

10 Claims, No Drawings

REACTIVE PHENOLIC ANTIOXIDANTS AND POLYESTERS REACTED THEREWITH

This invention pertains to certain novel phenolic antioxidant compounds and to polyester compositions having reacted therewith a stabilizing amount of at least one of the phenolic antioxidant compounds. More specifically, this invention concerns novel antioxidant compounds containing a hindered phenol moiety in combination with an isophthalic moiety.

Although polyesters are not as susceptible to oxidative degradation as are other classes of polymeric material such as polyolefins, certain polyesters are degraded by oxidation, particularly thermally-induced oxidation resulting from the polyester being exposed to high temperatures during the processing and/or use thereof. One class of polyesters which are especially susceptible to oxidative degradation are those in which the diol residues comprise glycol ether residues such as residues of poly(alkylene glycols).

Various phenolic compounds have been proposed as antioxidants for a wide variety of polymeric materials. The known phenolic compounds include compounds having one or more functional groups which render them reactive with polyesters. Certain of the phenolic antioxidants presently used commercially in polyesters have, in general, one or more deficiencies. Particularly significant disadvantages are the termination and branching of the polymer chains which are caused by the phenolic antioxidants. Branching to any significant degree often makes linear polyesters brittle and thus not suitable for many end uses. Branching also can make control of the molecular weight difficult. Any additive which causes chain termination also is disadvantageous because it slows the rate of the polymerization and limits the molecular weight that can be achieved.

We have discovered a novel class of reactive, phenolic antioxidant compounds which can be incorporated into the polymer backbone of polyesters to effectively inhibit oxidative degradation thereof and are stable, i.e., are not decomposed, at the elevated temperatures at which such polyesters are typically manufactured, processed and/or used. Our novel compounds exhibit good to excellent antioxidant properties over prolonged periods of time and do not affect detrimentally either the physical properties or the color of the polyesters with which they are copolymerized.

The novel antioxidant compounds provided by our invention have the general formula:

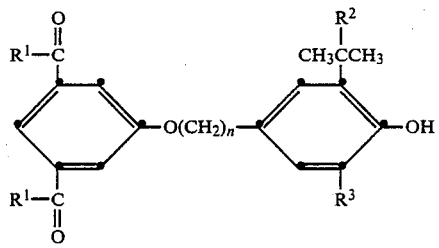

wherein $R^1$ is a residue capable of forming, under polyester-forming conditions, an ester group with the carbonyl group to which each $R^1$ is bonded and a hydroxy alkyl residue of a diol used in the formation of the polyester such as halogen, hydroxy or an unsubstituted or substituted alkoxy, cycloalkoxy or aryloxy;

$R^2$ is alkyl or aryl;

$R^3$ is alkyl or one of the groups having the formula

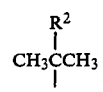

and n is 2 to about 6, most preferably 3.

Examples of the substituents which each $R^1$ may represent include chloro, bromo, hydroxy, unsubstituted or substituted alkoxy having up to about 12 carbon atoms such as methoxy, ethoxy, 2-hydroxyethoxy, 2-chloroethoxy, propyl, butoxy, isobutoxy, hexyloxy, 2-ethylhexyloxy, decyloxy, dodecyloxy, etc. and aryl radicals such as phenyl and phenyl substituted with alkyl radicals, e.g. containing up to about 8 carbon atoms, or with any of the aforesaid substituents. Generally, the $R^1$ substituents are not important since they are displaced when the phenolic compounds are copolymerized with, i.e., reacted into, the polyesters. The preferred $R^1$ substituents are hydroxy, methoxy, ethoxy and 2-hydroxyethoxy.

Examples of the alkyl groups represented by $R^2$ and $R^3$ include alkyl containing up to about 8 carbon such as methyl, ethyl, propyl, 2-propyl, butyl, 2-butyl, 2-methyl-2-propyl, 2,2-dimethylpropyl, pentyl, 2-pentyl, hexyl, 2-ethyl-hexyl, 2,4,4-trimethyl-2-pentyl, etc. The alkyl groups represented by $R^2$ and $R^3$ preferably contain up to 4 carbon atoms. The aryl group represented by $R^2$ may be unsubstituted phenyl or phenyl substituted with 1 or 2 groups selected from lower alkyl, i.e., alkyl containing up to about 4 carbon atoms, lower alkoxy or halogen, e.g., chlorine or bromine. The aryl group represented by $R^2$ preferably is unsubstituted phenyl.

The especially preferred reactive phenolic compounds provided by our invention have the formula

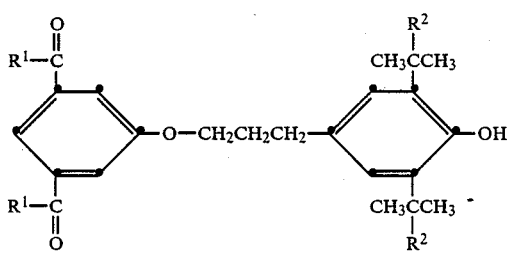

wherein $R^1$ is hydroxy, methoxy, ethoxy or 2-hydroxyethoxy and $R^2$ is alkyl or 1 to about 4 carbon atoms.

The polyesters susceptible to oxidative degradation which may be used in the preparation of our novel polyesters are comprised of:

(1) dicarboxylic acid residues comprising at least 50 mole percent, preferably at least 90 mole percent, terephthalic acid residues, 1,4-cyclohexanedicarboxylic acid residues, 2,6-naphthalenedicarboxylic acid or a mixture thereof; and (2) diol residues comprising (a) alkanediol residues having 4 to about 10 carbon atoms, (b) 1,4-cyclohexanedimethanol residues, (c) residue of a diol containing one or more ether linkages or (d) a mixture thereof.

Polyesters containing alkanediol residues of 4 to about 8 carbon atoms, e.g., butanediol residues, and/or 1,4-cyclohexanedimethanol residues typically are susceptible to oxidative degradation when such alkanediol and/or 1,4-cyclohexanedimethanol residues comprise at least 50 mole percent of the total diol residues. In contrast, the molar amount of diol residues (c) which may render a polyester susceptible to oxidative degradation can be relatively low, e.g., as low as 0.5 mole percent when the ether linkage-containing diol is of high molecular weight and thus contains a large number of ether linkages in each molecule.

Examples of diol residues (a) include the residues of 1,3- and 1,4-butanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,5-pentane-diol, 1,6-hexanediol, 1,8-octanediol, 1,10-decanediol and thiodiethanol. Examples of diol residues (c) include residues of poly(alkylene glycols) having molecular weights of up to about 3000 in which the alkylene residue contains 2 to 4 carbon atoms. Diethylene glycol, triethylene glycol, tetraethylene glycol, tripropylene glycol, poly(tetramethylene glycol) having a molecular weight in the range of about 200 to 3000, 1,3- and 1,4-bis(2-hydroxyethoxy)benzene are specific examples of diols containing ether linkages.

In addition to terephthalic acid, 1,4-cyclohexanedicarboxylic acid and/or 2,6-naphthalenedicarboxylic residues, diacid residues (1) may include residues of other dicarboxylic acids such as succinic, glutaric, adipic, azelaic, sebacic, fumaric, maleic, itaconic, 1,3-cyclohexanedicarboxylic, phthalic and/or isophthalic acid residues. Similarly, diol residues may include, in addition to diol residues (a), (b) and (c), other diol residues such as residues of propylene glycol, 1,3-propanediol and, especially, ethylene glycol. The linear polyesters also may contain minor amounts, e.g., up to about 4 mole percent, based on the total moles of diacid and diol residues, of tri- or tetra-functional reactants such as trimellitic anhydride and trimethylol propane.

The polyesters typically have an inherent viscosity (I.V., dl/g) of at least 0.5, e.g., about 0.5 to 1.5, preferably in the range of about 0.7 to 1.5, measured at 25° C. using 0.5 g polymer per 100 mL of a solvent consisting of 60 parts by weight phenol and 40 parts by weight tetrachloroethane. The number average molecular weight of the polyesters useful in our invention is in the range of about 15,000 to 50,000, preferably about 20,000 to 35,000. Typical polyesters which may be employed in our invention are described in U.S. Pat. Nos. 3,904,578, 3,989,664, 4,188,314, 4,349,469 and 4,510,205, Japanese Published Patent Application 97,049/78 and European Patent Application 150,454. The polyesters may contain other conventional polymer additives such as pigments, dyes, flame retardants, mold releasing agents, nucleating agents, lubricants, fillers, etc.

The polyesters susceptible to oxidative degradation which are preferred for our novel compositions comprise:

(1) dicarboxylic acid residues comprising at least 50 mole percent, preferably at least 90 mole percent, terephthalic acid residues, 1,4-cyclohexanedicarboxylic acid residues, 2,6-naphthalenedicarboxylic acid residues or a mixture thereof;

(2) diol residues comprising about 2 to 50 mole percent of residues of poly(tetramethylene glycol) having a molecular weight of about 200 to 3000, preferably 500 to 1500, and about 50 to 98 mole percent of alkanediol residues containing 2 to 4 carbon atoms, 1,4-cyclohexanedimethanol or a mixture thereof; and (3) up to about 2 mole percent, based on the total moles of (1) and (2) of the residues of trimellitic anhydride.

A particularly useful polyester has an inherent viscosity of about 0.8 to 1.5 and comprises:

(1) dicarboxylic acid residues consisting essentially of 1,4-cyclohexanedicarboxylic acid residues having a trans isomer content of at least 70 percent;

(2) diol residues consisting essentially of the residues of (i) 1,4-cyclohexanedimethanol and (ii) poly(tetramethylene glycol) having a molecular weight of about 500 to 1500, the mole ratio of (i):(ii) being in the range of about 60:40 to 97:3; and (3) up to about 0.75 mole percent, based on the total moles of (1) and (2), of the residue of a reactive compound containing at least 3 carboxyl or hydroxyl groups, preferably trimellitic anhydride.

The concentration of the residue of the antioxidant compound in the polyester can be varied substantially depending on a number of factors such as the oxidative stability of the particular polyester used, the particular end-use for which the polyester composition is intended and the like. Generally, a stabilizing amount of the antioxidant compound will be in the range of about 0.05 to 1.50 weight percent based on the weight of the polyester. Preferably, the concentration is in the range of about 0.10 to 0.50 weight percent (same basis).

The novel phenolic antioxidants provided by our invention may be prepared by a sequence of 3 reactions:

A. Reducing an alkyl arylalkanoate ester (II) with lithium aluminum hydride to obtain the corresponding alcohol (III):

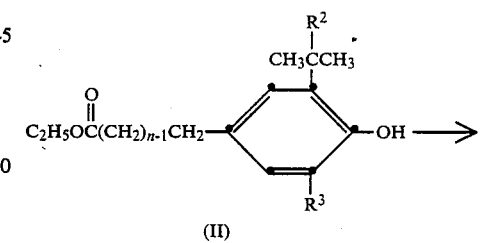

(II)

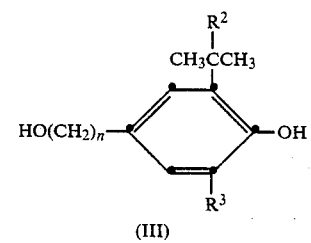

(III)

B. forming a sulfonate ester (IV) of the alcohol, and

C. reacting the sulfonate ester with a 5-hydroxyisophthalic compound (V) to obtain the reactive phenolic compounds of formula (I):

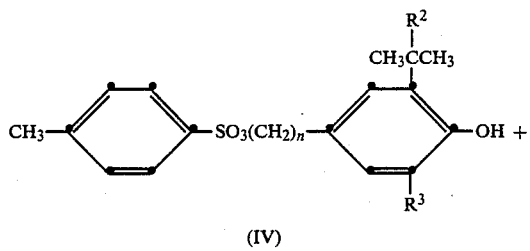

(IV)

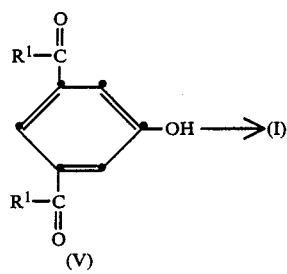

(V)

The polyester compositions provided by this invention may be prepared according to known esterification/polycondensation procedures by including one or more compounds of formula (I) at the commencement or during the polyester manufacturing process. For example, a mixture of one or more dicarboxylic acids, or ester-forming equivalents thereof, one or more diols and a reactive phenolic antioxidant of formula (I) may be heated in the presence of conventional esterification and/or poly-esterification catalysts at a temperature in the range of 150° to 300° C. and pressures of a few atmospheres to 0.2 torr. Normally, the dicarboxylic acid or derivative thereof is esterified or transesterified with the diol(s) at atmospheric pressure or slightly above and at a temperature at the lower end of the range specified. Polycondensation then is effected by increasing the temperature and lowering the pressure while removing excess diol from the mixture.

The preparation of the phenolic antioxidant compounds and polyester compositions of our invention is further illustrated by the following examples.

EXAMPLE 1

To a suspension lithium aluminum hydride (11.2 g) in diethyl ether (500 mL) is added over a period of 30 minutes ethyl 3-[3,5-bis(1,1-dimethylethyl)-4-hydroxyphenyl]propionate (60.0 g) in diethyl ether (100 mL). The mixture is heated at reflux for 3 hours and then quenched by the sequential addition of water (11 mL), 10% aqueous sodium hydroxide (11 mL) and water (66 mL). The resulting suspension is washed with tetrahydrofuran and the filtrate is concentrated to give 48 g of 3-[3,5-bis(1,1-dimethylethyl)-4-hydroxy-phenyl]-propanol. Trituration of the residue with heptane gave 46 g of light yellow crystals. The $^1$H NMR spectrum and field desorption mass spectrum are consistent with the above-specified product.

To a solution of 3-[3,5-bis-(1,1-dimethylethyl)-4-hydroxy-phenyl]propanol (5.3 g, 0.020 mol) in pyridine (50 mL) at 0° C. is added toluenesulfonyl chloride (4.2 g, 0.022 mol). The resulting solution is allowed to stand for 3 hours at 0° C. and then cold water is added and the sulfonate ester is extracted with methylene chloride. The organic layer is concentrated and one-half of the residue is combined with dimethyl 5-hydroxyisophthalate (2.1 g), dimethylformamide (50 mL) and potassium carbonate (2.0 g). This mixture is heated for 3 hours at 60°-80° C. The black reaction mixture is poured into 10% hydrochloric acid and the mixture is extracted with methylene chloride. The organic layer is concentrated and the residue obtained is crystallized from methanol twice to give 0.75 g of dimethyl 5-[3-[3,5-bis(1,1-dimethylethyl)-4-hydroxyphenyl]propoxy]isophthalate. The identity of the product is confirmed by $^1$H NMR, infrared and field desorption mass spectroscopy.

EXAMPLE 2

To a suspension lithium aluminum hydride (15.2 g) in tetrahydrofuran (500 mL) is added over a period of 60 minutes ethyl 3-[3-(1,1-dimethylethyl)-4-hydroxy-5-methylphenyl]propionate (80.0 g) in tetrahydrofuran (100 mL). The mixture is heated at reflux for 2 hours and then quenched by the sequential addition of water (17 mL), 10% aqueous sodium hydroxide (17 mL) and water (51 mL). The resulting suspension is washed with tetrahydrofuran and the filtrate is concentrated to give 40 g of crude 3-[3-(1,1-dimethylethyl)-4-hydroxy-5-methylphenyl]propanol. The crude intermediate is crystallized from heptane/toluene to give 38 g of light yellow crystals. The $^1$H NMR and field desorption spectra are consistent with the above-specified product.

To a solution of 3-[3-(1,1-dimethylethyl)-4-hydroxy-5-methylphenyl]propanol (22.2 g) in pyridine (200 mL) at 0° C. is added toluenesulfonyl chloride (22.8 g). The resulting solution is allowed to stand for 3 hours at 0° C. and then cold water is added and the sulfonate ester is extracted with methylene chloride. The organic layer is concentrated and the residue is combined with dimethyl 5-hydroxyisophthalate (35 g), dimethyl-formamide (300 mL) and potassium carbonate (50 g). This mixture is heated for 1.5 hours at 60°-80° C. The black reaction mixture is poured into 10% hydrochloric acid and the mixture is extracted with methylene chloride. The organic layer is extracted with 10% aqueous sodium hydroxide and then concentrated. The residue obtained is distilled twice at 300° C. and 0.05 torr to give a light yellow glass. NMR, infrared and field desorption mass spectroscopy confirm that the product obtained is dimethyl 5-[3-[3-(1,1-dimethylethyl)-4-hydroxy-5-methylphenyl]propoxy]isophthalate.

The compounds set forth in the following Table conform to formula (I) wherein n is 3 and may be prepared by reducing the appropriate alkyl hydroxyphenylpropionate (II), reacting the hydroxyphenylpropanol (III) obtained with toluenesulfonyl chloride and reacting the resulting sulfonate ester (IV) with the appropriate 5-hydroxyisophthalic compound according to the procedure described in the preceding examples.

TABLE I

| Example | $R^1$ | $R^2$ | $R^3$ |
| --- | --- | --- | --- |
| 3 | —OH | —CH$_3$ | —C(CH$_3$)$_3$ |
| 4 | —OH | —CH$_3$ | —CH$_3$ |
| 5 | —OC$_2$H$_5$ | —CH$_3$ | —C(CH$_3$)$_3$ |
| 6 | —OC$_2$H$_5$ | —CH$_3$ | —CH$_3$ |
| 7 | —CH$_2$CH$_2$OH | —CH$_3$ | —C(CH$_3$)$_3$ |
| 8 | —CH$_2$CH$_2$OH | —CH$_3$ | —CH$_3$ |
| 9 | —OCH$_3$ | —C$_2$H$_5$ | —C(CH$_3$)$_2$C$_2$H$_5$ |
| 10 | —OCH$_3$ | —CH$_3$ | —C$_2$H$_5$ |
| 11 | —OCH$_3$ | —C$_6$H$_5$ | —C(CH$_3$)$_2$C$_6$H$_5$ |
| 12 | —OCH$_3$ | —CH$_3$ | —CH(CH$_3$)$_2$ |

EXAMPLE 13

The following materials are placed in a 500 mL, single-neck flask equipped with a metal stirrer, nitrogen inlet and volatiles outlet:

59.7 g (0.299 mol) dimethyl 1,4-cyclohexanedicarboxylate,
40.5 g (0.273 mol) 1,4-cyclohexanedimethanol,
26.7 g (0.0267 mol) poly(tetramethylene glycol) having an average molecular weight of 1000,
0.29 g (0.0015 mol) trimellitic anhydride,
0.32 g of the phenolic antioxidant of Example 1, and
0.0075 g Ti from a 1-butanol solution of titanium tetraisopropoxide.

The flask and contents are heated with stirring under nitrogen at 220° C. in a Belmont metal bath for 60 minutes. After increasing the reaction temperature to 270° C., the nitrogen purge is replaced with a vacuum source and the pressure is reduced to less than 0.3 torr for a period of 20 to 40 minutes. The polyester thus produced crystallizes upon cooling the reaction mixture. The polyester has an inherent viscosity of 1.150 dl/g.

EXAMPLE 14

The procedure of Example 13 is repeated using the phenolic antioxidant dimethyl 5-[3-[3-(1,1-dimethylethyl)-4-hydroxy-5-methylphenyl]propoxy]isophthalate (0.30 g) in place of the antioxidant used in Example 13. The polymer obtained has an inherent viscosity of 1.037 dl/g.

COMPARATIVE EXAMPLE 1

The procedure of Example 13 is repeated except that the phenolic antioxidant compound is omitted. The polymer obtained has an inherent viscosity of 1.261 dl/g.

COMPARATIVE EXAMPLE 2

The procedure of Example 13 is repeated using the commercial antioxidant 2,2-bis[[3-[3-[3,5-bis(1,1-dimethylethyl)-4-hydroxyphenyl]-1-oxopropoxy]methyl]-1,3-propanediyl 3,5-bis(1,1-dimethylethyl)-4-hydroxybenzenepropanoate (Irganox 1010, 0.21 g–0.2 weight percent based on the weight of the polymer obtained). The polyester has an inherent viscosity of 1.069 dl/g.

Polymers from Examples 13 and 14 and Comparative Examples 1 and 2 are ground through a 4 mm screen and dried in a vacuum oven at 65° to 70° C. for 16 hours. Samples (approximately 3.0 g) of each of the dry polymers are placed between two silicon-treated plates and compression molded into a plurality of round, 10 mil-thick film at 225° C. using a Hannifin press and a 20 second mold time. A sample of each film is submitted for measurement of inherent viscosity and the remaining film samples are placed in a forced-air oven at 130° C. and equipped with a rotating carousel which provides uniform heating of the samples. To monitor the rate of polymer oxidation as shown by a decrease in the polymer inherent viscosity, samples of the film are removed from the oven periodically and the inherent viscosity is determined.

The oxidative degradation of the film samples of the polyesters of Examples 13 and 14 and Comparative Examples 1 and 2 (C-1 and C-2) are shown in Table II wherein the inherent viscosity (I.V., dl/g) both before and after ageing the film prepared from each polymer for the hours specified is set forth. The percent loss in inherent viscosity (I.V. Loss) based on the inherent viscosity of the initial film also is set forth.

TABLE II

| Example | Hours Aged | Film I.V. | I.V. Loss |
|---|---|---|---|
| 13 | 0 | 1.132 | 0.0 |
|  | 88 | 1.000 | 11.7 |
|  | 142 | 0.828 | 26.9 |
|  | 190 | 0.684 | 39.6 |
| 14 | 0 | 1.107 | 0.0 |
|  | 5 | 1.069 | 3.4 |
|  | 24 | 0.983 | 11.2 |
|  | 29 | 0.900 | 18.7 |
|  | 48 | 0.298 | 73.1 |
| C-1 | 0 | 1.257 | 0.0 |
|  | 5 | 0.502 | 60.1 |
|  | 8 | 0.273 | 78.3 |
| C-2 | 0 | 1.065 | 0.0 |
|  | 88 | 0.968 | 9.2 |
|  | 142 | 0.900 | 15.5 |
|  | 190 | 0.804 | 24.5 |

The invention has been described in detail with particular reference to preferred embodiments thereof, but it will be understood that variations and modifications will be effected within the spirit and scope of the invention.

We claim:

1. A compound having the formula

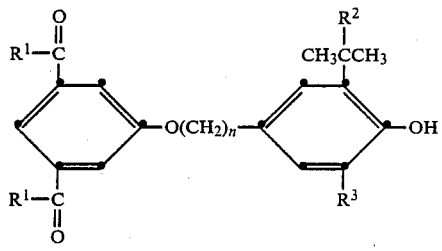

wherein
$R^1$ is a residue capable of forming, under polyester-forming conditions, an ester group with the carbonyl group to which each $R^1$ is bonded and a hydroxy alkyl residue of a diol used in the formation of the polyester;
$R^2$ is alkyl or aryl;
$R^3$ is alkyl or one of the groups having the formula

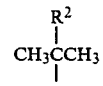

and
n is 2 to about 6.

2. A compound according to claim 1 wherein $R^1$ is chloro, bromo, hydroxy, an unsubstituted or substituted alkoxy group containing 1 to about 12 carbon atoms or an unsubstituted or substituted phenoxy group.

3. A compound according to claim 1 having the formula

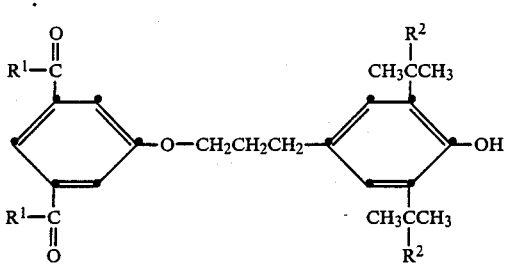

wherein

R¹ is hydroxy, methoxy, ethoxy or 2-hydroxyethoxy; and

R² is alkyl of 1 to about 4 carbon atoms.

4. A polymer composition comprising a polyester normally susceptible to oxidative degradation having an inherent viscosity of at least about 0.5 measured at 25° C. using 0.5 g polymer per 100 mL of a solvent consisting of 60 parts by weight phenol and 40 parts by weight tetrachloroethane and comprised of (1) dicarboxylic acid residues comprising at least 50 mole percent terephthalic acid residues, 1,4-cyclohexanedicarboxylic acid residues, 2,6-naphthalenedicarboxylic acid residues or a mixture thereof; and (2) diol residues comprising (a) alkanediol residues having 4 to about 10 carbon atoms, (b) 1,4-cyclohexanedimethanol residues, (c) residue of a diol containing ether linkages or (d) a mixture thereof;

having copolymerized therein the residue of a compound having the formula

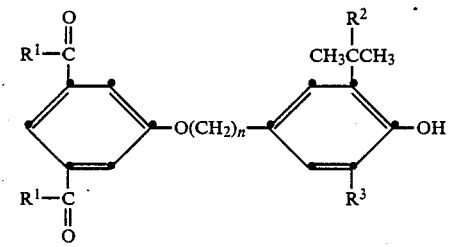

wherein

R¹ is a residue capable of forming, under polyester-forming conditions, an ester group with the carbonyl group to which each R¹ is bonded and a hydroxy alkyl residue of a diol used in the formation of the linear polyester;

R² is alkyl or aryl; and

R³ is alkyl or one of the groups having the formula

n is 2 to about 6.

5. A polymer composition comprising a polyester normally susceptible to oxidative degradation having a number average molecular weight of about 15,000 to 35,000 and comprised of (1) dicarboxylic acid residues comprising at least 90 mole percent terephthalic acid residues, 1,4-cyclohexanedicarboxylic acid residues, 2,6-naphthalenedicarboxylic acid residues or a mixture thereof; and (2) diol residues comprising at least 50 mole percent alkanediol residues containing 4 to about 8 carbon atoms, 1,4-cyclohexanedimethanol residues or a mixture thereof;

having copolymerized therein about 0.05 to 1.50 weight percent based on the weight of the polyester of the residues of a compound having the formula

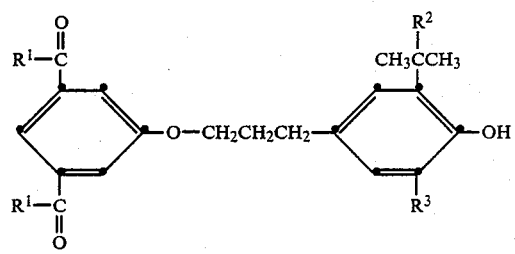

wherein

R¹ is chloro, bromo, hydroxy, an unsubstituted or substituted alkoxy group containing 1 to about 12 carbon atoms or an unsubstituted or substituted phenoxy group;

R² is alkyl or aryl; and

R³ is alkyl or one of the groups having the formula

6. A polymer composition comprising the polyester of claim 5 having copolymerized therein about 0.1 to 0.5 weight percent of the residue of a compound having the formula

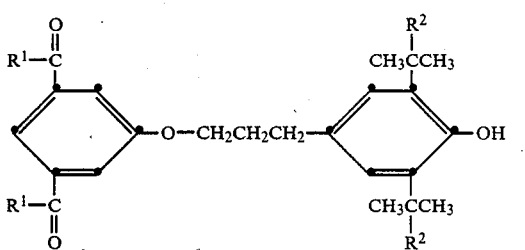

wherein

R¹ is hydroxy, methoxy, ethoxy or 2-hydroxyethoxy; and

R² is alkyl of 1 to about 4 carbon atoms.

7. A polymer composition comprising a polyester normally susceptible to oxidative degradation having a number average molecular weight of about 15,000 to 35,000 and comprised of (1) dicarboxylic acid residues comprising at least 90 mole percent terephthalic acid residues, 1,4-cyclohexanedicarboxylic acid residues, 2,6-naphthalenedicarboxylic acid residues or a mixture thereof;

(2) diol residues comprising about 2 to 50 mole percent of residues of poly(tetramethylene glycol) having a molecular weight of about 200 to 3000 and about 50 to 98 mole percent of alkanediol residues containing 2 to 4 carbon atoms, 1,4-cyclohexanedimethanol or a mixture thereof; and (3) up to about 2 mole percent, based on the total moles of (1) and (2) of the residues of trimellitic anhydride;

having copolymerized therein about 0.05 to 1.50 weight percent based on the weight of the polyester of the residues of a compound having the formula

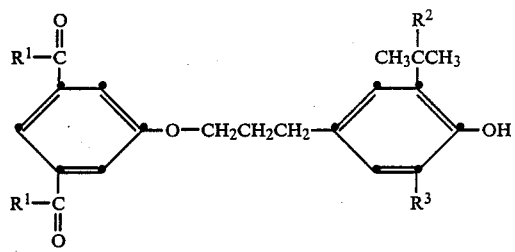

wherein
$R^1$ is chloro, bromo, hydroxy, an unsubstituted or substituted alkoxy group containing 1 to about 12 carbon atoms or an unsubstituted or substituted phenoxy group;
$R^2$ is alkyl or aryl; and
$R^3$ is alkyl or one of the groups having the formula

8. A polymer composition comprising the polyester of claim 7 having copolymerized therein about 0.1 to 0.5 weight percent of the residue of a compound having the formula

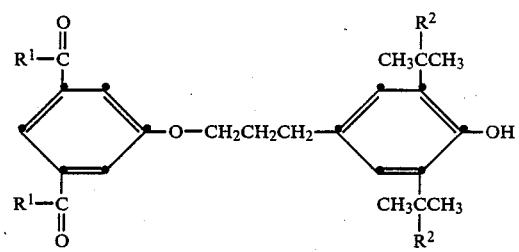

wherein
$R^1$ is hydroxy, methoxy, ethoxy or 2-hydroxyethoxy; and
$R^2$ is alkyl of 1 to about 4 carbon atoms.

9. A polymer composition comprising a polyester normally susceptible to oxidative degradation having a number average molecular weight of about 15,000 to 35,000 and comprised of (1) dicarboxylic acid residues consisting essentially of 1,4-cyclohexanedicarboxylic acid residues having a trans isomer content of at least 60 percent;

(2) diol residues consisting essentially of the residues of (i) 1,4-cyclohexanedimethanol and (ii) poly(tetramethylene glycol) having a molecular weight of about 500 to 1500, the mole ratio of (i):(ii) being in the range of about 60:40 to 97:3; and (3) up to about 0.75 mole percent, based on the total moles of (1) and (2), of the residue of of a reactive compound containing at least 3 carboxyl or hydroxyl groups;

having copolymerized therein about 0.05 to 1.50 weight percent based on the weight of the polyester of the residue of a compound having the formula

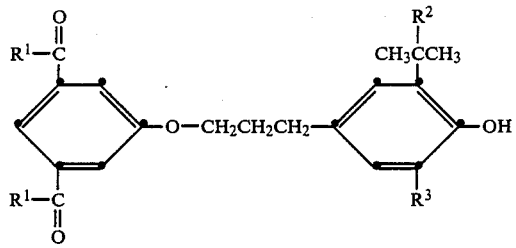

wherein
$R^1$ is chloro, bromo, hydroxy, an unsubstituted or substituted alkoxy group containing 1 to about 12 carbon atoms or an unsubstituted or substituted phenoxy group;
$R^2$ is alkyl or aryl; and
$R^3$ is alkyl or one of the groups having the formula

10. A polymer composition comprising the polyester of claim 9 having copolymerized therein about 0.1 to 0.5 weight percent of the residue of a compound having the formula

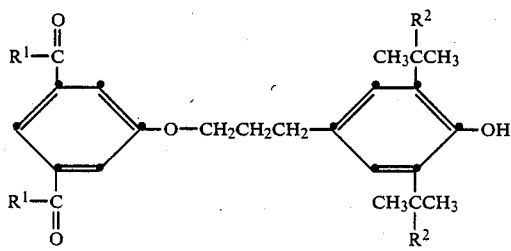

wherein
$R^1$ is hydroxy, methoxy, ethoxy or 2-hydroxyethoxy; and
$R^2$ is alkyl of 1 to about 4 carbon atoms.

* * * * *